(12) United States Patent
Yang (10) Patent No.: US 12,102,792 B2
(45) Date of Patent: Oct. 1, 2024

(54) BILATERALLY DRIVEN DRUG INFUSION DEVICE WITH MULTIPLE INFUSION MODES

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 572 days.

(21) Appl. No.: 17/431,426

(22) PCT Filed: May 14, 2020

(86) PCT No.: PCT/CN2020/090152
§ 371 (c)(1),
(2) Date: Aug. 17, 2021

(87) PCT Pub. No.: WO2020/233486
PCT Pub. Date: Nov. 26, 2020

(65) Prior Publication Data
US 2022/0118176 A1    Apr. 21, 2022

(30) Foreign Application Priority Data

May 17, 2019 (WO) ................ PCT/CN2019/087342
Aug. 1, 2019 (WO) ................ PCT/CN2019/098784

(51) Int. Cl.
*A61M 5/145* (2006.01)
*A61M 5/14* (2006.01)
(Continued)

(52) U.S. Cl.
CPC ............ *A61M 5/1452* (2013.01); *A61M 5/14* (2013.01); *A61M 5/14236* (2013.01);
(Continued)

(58) Field of Classification Search
CPC .. A61M 5/14; A61M 5/1452; A61M 5/14236; A61M 5/14248; A61M 5/16804;
(Continued)

(56) References Cited

U.S. PATENT DOCUMENTS

2005/0238507 A1* 10/2005 Dilanni ..................... F04B 9/08
417/415
2008/0319394 A1   12/2008 Yodfat et al.
(Continued)

FOREIGN PATENT DOCUMENTS

| CN | 101208515 | 6/2008 |
| CN | 106999670 | 8/2017 |

(Continued)

OTHER PUBLICATIONS

"Search Report of Europe Counterpart Application", issued on Jun. 20, 2023, p. 1-p. 8.

(Continued)

*Primary Examiner* — Scott J Medway
*Assistant Examiner* — Anh Bui
(74) *Attorney, Agent, or Firm* — JCIP GLOBAL INC.

(57) ABSTRACT

A bilaterally driven drug infusion device with multiple infusion modes comprises: a drug storage unit (150); a piston (160) and a driving wheel (130,630) respectively connected with a screw (170), the driving wheel (130,630), provided with wheel teeth (131,631), drives the screw (170) movement by rotation, the piston (160) is arranged in the drug storage unit (150), the screw (170) advances the piston (160) to move; a driving unit (100,200,300,400,500,600) cooperating with the driving wheel (130,630); and a power unit (180,680), connected to the driving unit (100,200,300, 400,500,600), outputs forces in two different directions (A',B') on the driving unit (100,200,300,400,500,600) to lead driving unit (100,200,300,400,500,600) to perform (Continued)

multiple-mode operation, making the infusion device have multiple infusion increments or infusion rates. The driving unit (100,200,300,400,500,600) has a variety of different pivot amplitudes, that is, the driving unit (100,200,300,400, 500,600) can realize multiple-mode pivot, thereby achieving increment-adjustable infusion.

13 Claims, 8 Drawing Sheets

(51) Int. Cl.
*A61M 5/142* (2006.01)
*A61M 5/168* (2006.01)
*A61M 5/172* (2006.01)
*G16H 20/17* (2018.01)

(52) U.S. Cl.
CPC .... *A61M 5/14248* (2013.01); *A61M 5/16804* (2013.01); *A61M 5/172* (2013.01); *G16H 20/17* (2018.01); *A61M 2005/14208* (2013.01); *A61M 2005/14506* (2013.01); *A61M 2205/3327* (2013.01); *A61M 2205/36* (2013.01); *A61M 2230/201* (2013.01)

(58) Field of Classification Search
CPC .............. A61M 5/172; A61M 5/16877; A61M 5/31536; A61M 2005/14208; A61M 2005/14506; A61M 2205/10
See application file for complete search history.

(56) References Cited

U.S. PATENT DOCUMENTS

| | | |
|---|---|---|
| 2017/0095610 A1 | 4/2017 | Holmes et al. |
| 2017/0326301 A1* | 11/2017 | Butler ............... A61M 5/31536 |
| 2019/0117881 A1 | 4/2019 | Yang |

FOREIGN PATENT DOCUMENTS

| | | |
|---|---|---|
| CN | 107456625 | 12/2017 |
| CN | 109451730 | 3/2019 |

OTHER PUBLICATIONS

"International Search Report (Form PCT/ISA/210) of PCT/CN2020/090152," mailed on Jul. 30, 2020, pp. 1-2.

* cited by examiner

BILATERALLY DRIVEN DRUG INFUSION DEVICE WITH MULTIPLE INFUSION MODES

CROSS-REFERENCE TO RELATED APPLICATION

This application is a 371 of international application of PCT application serial no. PCT/CN2020/090152, filed on May 14, 2020, which claims the priority benefit of PCT application no. PCT/CN2019/087342, filed on May 17, 2019 and the priority benefit of PCT application no. PCT/CN2019/098784, filed on Aug. 1, 2019. The entirety of each of the above mentioned patent applications is hereby incorporated by reference herein and made a part of this specification.

TECHNICAL FIELD

The present invention mainly relates to the field of medical instruments, in particular to a bilaterally driven drug infusion device with multiple infusion modes.

BACKGROUND

A bilaterally driven drug infusion device with multiple infusion modes is a medical device that achieves treatment of a patient's physiological condition by continuously injecting a drug into a patient. Bilaterally driven drug infusion device with multiple infusion modes are widely used for the treatment of diabetes, allowing required doses of insulin to be continuously infused into the subcutaneous tissue of the patient's body, thereby simulating the secretion function of the pancreas, thereby keeping the patient's blood sugar stable. The drug fluid is usually stored inside the infusion pump. The existing bilaterally driven drug infusion device with multiple infusion modes usually attaches the pump body directly to the patient's body through a medical adhesive tape, and the patient operates a remote device to control infusion.

In the case of drug infusion, the current infusion devices can only operate with one level of increment, therefore, the infusion process cannot be flexibly controlled, and the infusion efficiency is relatively low. Moreover, the minimum dose that can be infused each time is relatively large, which can cause the concentration of some substance(s) in a patient's body fluid to fluctuate greatly under the control of the infused drug, and cannot achieve the purpose of more accurately controlling the concentration of that substance(s).

Therefore, there is a need in the prior art for a bilaterally driven drug infusion device with multiple infusion modes that can flexibly control a drug infusion process and improve drug infusion efficiency.

BRIEF SUMMARY OF THE INVENTION

The embodiment of the invention discloses a bilaterally driven drug infusion device with multiple infusion modes. The driving unit has multiple-mode operation, thus realizing driving the driving wheel in multiple-mode rotations and making the infusion device have multiple infusion increments or infusion rates. The user can flexibly control the infusion process, which improves the infusion efficiency.

The invention discloses a bilaterally driven drug infusion device with multiple infusion modes, comprising: a drug storage unit; a piston and a driving wheel respectively connected with a screw, the driving wheel, provided with wheel teeth, drives the screw movement by rotation, the piston is arranged in the drug storage unit, the screw advances the piston to move; a driving unit cooperating with the driving wheel; and a power unit, connected to the driving unit, outputs forces in two different directions on the driving unit to lead driving unit to perform multiple-mode operation, making the infusion device have multiple infusion increments or infusion rates.

According to an aspect of the present invention, the multiple-mode operation of the driving unit includes the movement amplitude or the movement rate, therefore, the different multiple-mode operations of the driving unit include multiple different movement amplitudes or multiple different movement rates.

According to an aspect of the present invention, it further includes a pivot shaft, and the driving unit includes at least two driving arms, and the driving unit pivots around the pivot shaft to drive driving arms to move.

According to an aspect of the present invention, the driving wheel includes at least two sub-wheels, and the driving arm rotates the driving wheel by engaging the wheel teeth.

According to an aspect of the present invention, the pivot shaft is disposed between the two sub-wheels, one or more driving arms are respectively disposed on both sides of the driving unit, and each sub-wheel cooperates with at least one driving arm.

According to an aspect of the present invention, one movement amplitude corresponds to one kind of pivot mode of the driving unit, and the driving unit, pivoting in various pivot modes, drives the driving arm to rotate the driving wheel to implement increment-adjustable infusion, and each increment-adjustable infusion corresponds to an infusion increment.

According to an aspect of the present invention, multiple-mode pivot of the driving unit includes:
after pivoting one or more steps in one direction in a single time, the driving unit starts pivoting one or more steps in another direction until the end of the pivot in this direction, the driving unit completes an alternate pivot in both directions to perform multiple-mode driving on the driving wheel.

According to an aspect of the present invention, two driving arms are installed on each side of the driving unit, and two driving arms on one side of the driving unit are installed up and down, or are installed left and right.

According to an aspect of the present invention, the horizontal distance between the driving ends of the two driving arms on one side of the driving unit is h, the pitch of the wheel teeth is s, $0.1\ s \leq h \leq 2.5\ s$.

According to an aspect of the present invention, $0.5\ s \leq h \leq 1.5\ s$.

According to an aspect of the present invention, the wheel teeth are ratchet teeth, and during the whole process of driving unit pivoting in one direction, the driving unit alternately pivots and stops for multiple times to drive driving arms to alternately engage and stop engaging the ratchet teeth, so that the driving wheel alternately rotates and stops rotation to perform tooth number adjustable rotation.

According to an aspect of the present invention, when the driving unit drives the driving wheel, at least one of the driving arms on one side engages the wheel teeth, while the driving arm on the other sides of the driving unit slide on the wheel teeth.

According to an aspect of the present invention, multiple-mode pivots of driving unit include a large mode and a small mode, and when the infusion is performed, the driving unit can switch between the large mode and the small mode to realize increment-adjustable infusion.

According to an aspect of the present invention, multiple-mode pivot of the driving unit further comprise: one or more intermediate modes, wherein the intermediate mode is between the large mode and the small mode, and the driving unit can switch among the large mode, the intermediate mode and the small mode to achieve the increment-adjustable infusion.

According to an aspect of the present invention, it further includes a base on which the driving wheel is movably assembled, and the base and the driving wheel are frictional fit, and the driving wheel stops rotating when the driving arm is sliding on the surface of the wheel teeth.

According to an aspect of the present invention, it further includes a position limited member which is movably assembled on the base to limit the position of the driving wheel, and the position limited member and the driving wheel are frictional fit, and the driving wheel stops rotating when all of the driving arms are sliding on the surface of the wheel teeth.

Compared with the prior art, the technical solution of the present invention has the following advantages:

In the bilaterally driven drug infusion device with multiple infusion modes disclosed by the present invention, the power unit outputs forces in two different directions on the driving unit to lead driving unit to perform multiple-mode operation, making the infusion device have multiple infusion increments or infusion rates. The driving unit has a variety of different pivot amplitudes, that is, the driving unit can realize multiple-mode pivot, thereby achieving increment-adjustable infusion. In addition, the driving unit also includes various movement rates, which makes the infusion process more flexible and controllable and significantly improves the efficiency of drug infusion. At the same time, this invention also reduces the minimum drug infusion dosage, accurately controls the process of the drug infusion, effectively avoids large fluctuations of concentration of some substance(s) in patient's body fluid and enables the patients to control and manage their physiological condition more precisely.

Furthermore, multiple-mode pivot of the driving unit includes a large mode and a small mode. Patients can freely choose and switch the large mode or the small mode to infuse according to the actual infusion volume and infusion rate requirements, making the infusion process more flexible and controllable, greatly improving the infusion efficiency.

Furthermore, multiple-mode pivot of the driving unit includes large mode and small mode. Patients can freely choose and switch large mode or small mode infusion according to the actual infusion volume and infusion rate requirements, making the infusion process more flexible and controllable, greatly improving the infusion efficiency.

Furthermore, a plurality of movement modes of the driving unit further comprise: one or more intermediate modes. Setting intermediate modes provides more infusion options for the patient and the patient's control of the infusion process is more flexible.

Furthermore, the infusion device further includes a base which is frictional fit with the driving wheel. The driving wheel stops rotating when the driving arm is sliding on the surface of the wheel teeth, improving the accuracy of drug infusion and eliminating potential safety hazards.

DETAILED DESCRIPTION

As previously mentioned, prior art infusion devices have only one unadjustable infusion mode and do not have the flexibility to control the infusion process.

It has been found through research that the above mentioned problems are caused by the fact that the driving unit in the prior art infusion device has only one operating mode (or only one pivot mode), which results in a relatively simple control of the infusion process in the prior art.

In order to solve this problem, the present invention provides a bilaterally driven drug infusion device with multiple infusion modes in which a driving unit has multiple-mode operation to perform tooth-number adjustable driving on the driving wheel. The different options of increment allow patients to flexibly control the drug infusion process. At the same time, the minimum drug infusion amount of the infusion device is effectively reduced, and the fluctuation of concentration of some substance(s) in patient's body fluid is mitigated.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

Figure 1:
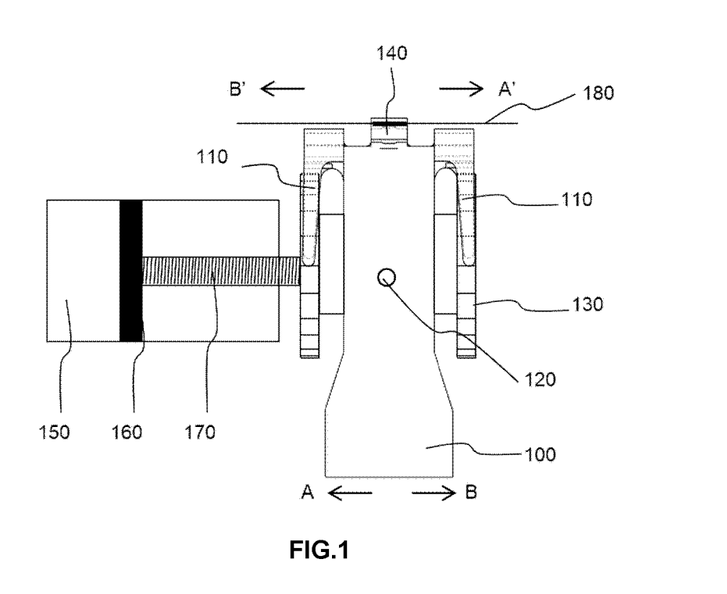
FIG. 1 is a top view of a drug storage unit, a piston, a screw, a driving unit, a power unit, and a driving wheel in a bilaterally driven drug infusion device with multiple infusion modes according to an embodiment of the present invention.

FIG. 1 is a top view of an infusion device according to an embodiment of the present invention. The infusion device includes a driving unit 100, a driving wheel 130, a drug storage unit 150, a piston 160, a screw 170, and a power unit 180.

The screw 170 is coupled to the piston 160 and the driving wheel 130, respectively. In the embodiment of the present invention, the driving wheel 130 is movably mounted on the device base 190, and the driving wheel 130 moves the driving screw 170 through rotation to advance the piston 160 disposed in the drug storage unit 150 to move forward for the purpose of injecting drugs.

The driving unit 100 cooperates with the driving wheel 130. Here, the cooperation means that the movements of both the driving unit 100 and the driving wheel 130 are interrelated to each other.

Figure 6:
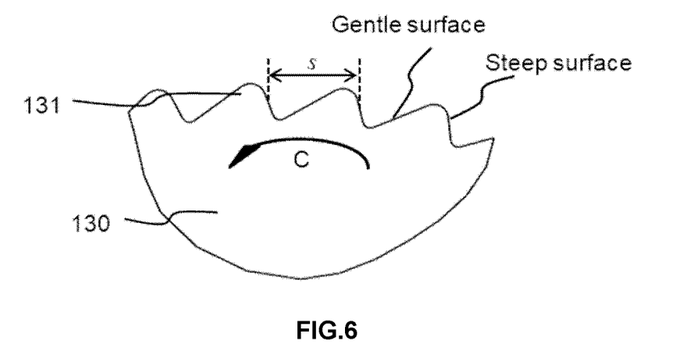
FIG. 6 is a partial schematic structural view of a driving wheel in a bilaterally driven drug infusion device with multiple infusion modes according to an embodiment of the present invention.
Figure 7:
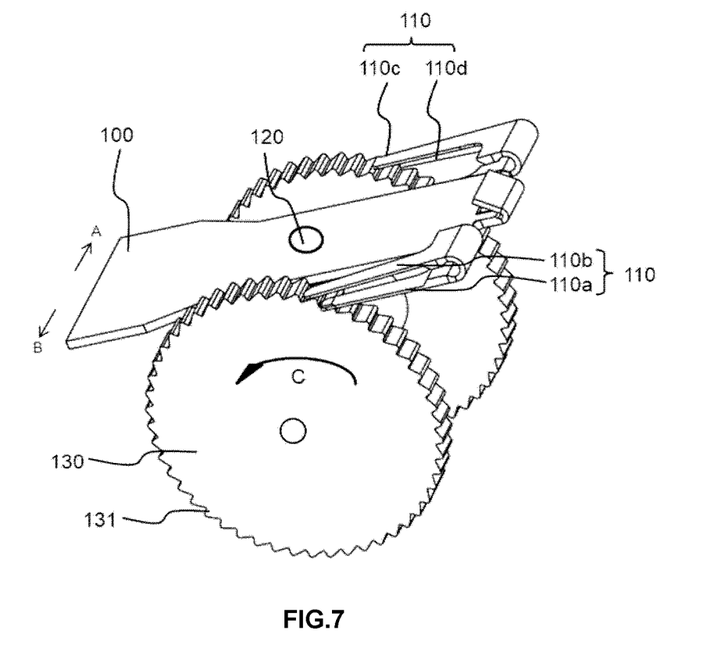
FIG. 7 is a schematic structural view of a driving unit engaging a driving wheel in a bilaterally driven drug infusion device with multiple infusion modes according to an embodiment of the present invention.

In the embodiment of the present invention, the driving wheel 130 is provided with wheel teeth 131 (as shown in FIG. 6 and FIG. 7). The driving unit 100 is movably connected to the base 190 through a pivot shaft 120, and the driving unit 100 can pivot around the rotating shaft 120. The driving unit 100 includes at least two driving arms 110. The pivoting driving unit 100 drives the driving arm 110 to engage the wheel teeth 131 forward to rotate the driving wheel 130.

The power unit 180 outputs two different directional forces on the driving unit 100, making the driving unit 100 have different multiple-mode operation. Here, the operation mode includes the amplitude or rate of the movement. Therefore, the multiple-mode operation of the driving unit 100 includes various movement amplitudes or movement rates, which will be described in detail below.

Specifically, in the embodiment of the present invention, the power unit 180 is fixedly connected at the top position 140 of the driving unit 100, thereby dividing the power unit 180 into two left and right portions, such as the A' direction portion and the B' direction portion in FIG. 1. The driving unit 100 is alternately led to pivot in the A' direction or the B' direction through the pivot shaft 120. Specifically, in the embodiment of the present invention, when the power unit 180 leads the driving unit 100 to A' direction, the driving unit 100 pivots in A direction through the pivot shaft 120. When the power unit 180 leads the driving unit 100 in the B' direction, the driving unit 100 pivots in B direction through the pivot shaft 120. By alternately leading the driving unit 100 in A' direction and B' direction, the driving unit 100 can alternately pivot through the pivot shaft 120 in the A direction and the B direction.

Specifically, in the embodiment of the present invention, the power unit 180 is made of shape memory alloy. The A' direction portion and the B' direction portion of the shape memory alloy are alternately powered on and off, and a leading force is applied to the driving unit 100 by a change in the length of the power unit 180 thereof. The power unit 180 may be composed of one piece of shape memory alloy, or may be composed of left and right segments (such as the A' direction segment and the B' direction segment) of shape memory alloy, and is not specifically limited herein, as long as the force can be applied to lead the driving unit 100 pivot.

Here, it should be noted that the power unit 180 includes but is not limited to a shape memory alloy. In other embodiments of the present invention, the power unit 180 may also be other structures, and the location where the power unit 180 applies force to the driving unit 100 is also not limited to the top position 140, as long as the action of applying a force to the driving unit 100 can be satisfied to cause the driving unit 100 to alternately pivot left and right.

Obviously, by controlling the magnitude of the power output by the power unit 180, the driving unit 100 will have various movement amplitudes. As in the embodiment of the present invention, by controlling the magnitude of the current, the length of the shape memory alloy will change, changing the magnitude of the power and the movement amplitude of the driving unit 100. Therefore, the driving unit 100 has various movement amplitudes. One movement amplitude of the driving unit 100 corresponds to one kind of pivot mode, and therefore, the driving unit 100 has multiple-mode pivot.

Similarly, by controlling the frequency of the power output by the power unit 180, the driving unit 100 will have various movement rates. As in the embodiment of the present invention, by changing the energization frequency, the frequency of the power output also changes, thus changing the movement rate of the driving unit 100 accordingly.

Figure 2A:
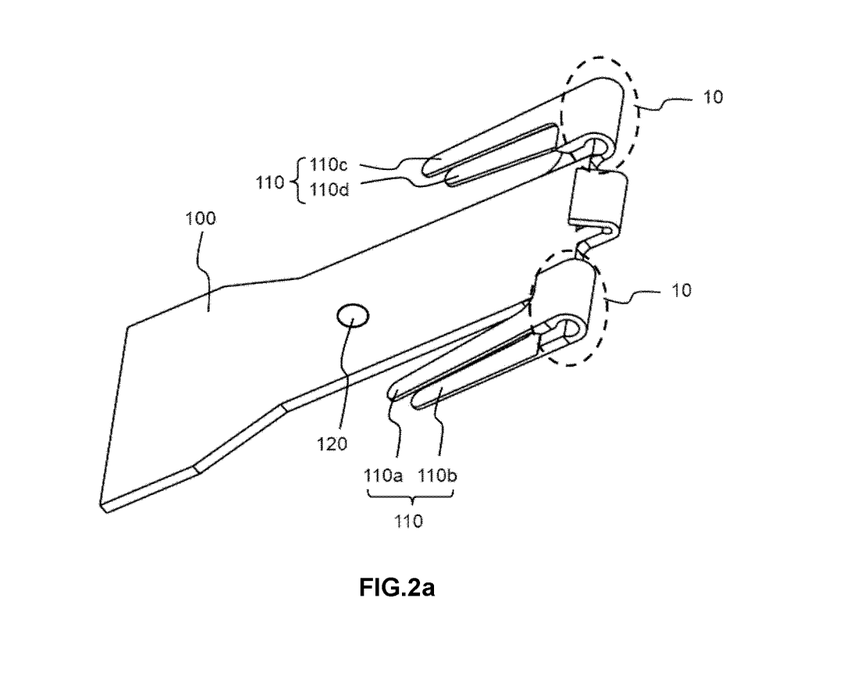
FIG. 2a-FIG. 2c are respectively a schematic structural view of a three-dimensional structure, a side view and a top view of a driving unit in a bilaterally driven drug infusion device with multiple infusion modes according to an embodiment of the present invention.

Referring to the perspective view of the driving unit 100 shown in FIG. 2a, the driving unit 100 further includes more than two driving arms 110. The driving wheel 130 includes a plurality of sub-wheels. Referring to the structure shown in FIG. 1 and FIG. 2a, when a plurality of driving arms 110 are installed on one side of the driving unit 100, the driving unit 100 can drive the driving arms 110 to engage the wheel teeth 131 through adjustable pivoting to rotate the driving wheel 130 by an optional number of teeth. Thus, in an embodiment of the invention, the driving unit 100 and the driving wheel 130 are designed to work compatibly, which means that the position of the driving wheel 130 and the number of the sub-wheels need to be compatible with the working principle of the driving unit 100 and the number, position and structure of the driving arms 110.

As shown in FIG. 1 and FIG. 2a, in the embodiment of the present invention, a plurality of driving arms 110 are installed on each side of the driving unit 100. Therefore, a plurality of sub-wheels are also installed on both sides of the driving unit 100 to cooperate with the driving arms 110. Specifically, in the embodiment of the present invention, the driving unit 100 includes four driving arms 110, which are 110a, 110b, 110c, and 110d, respectively. 110a, 110b are installed on one side of the driving unit 100, while 110c, 110d are installed on the other side of the driving unit 100. The driving wheel 130 includes two sub-wheels, one of which cooperates with 110a, 110b and the other of which cooperates with 110c, 110d.

It should be noted that the driving wheel 130 may further include more than two sub-wheels. For example, according to the design of the position and structure of the plurality of driving arms 110, two adjacent sub-wheels may be set on one side of the driving unit 100 to cooperate with different positions, numbers of driving arms 110 on this side of the driving unit 100.

Figure 2B:
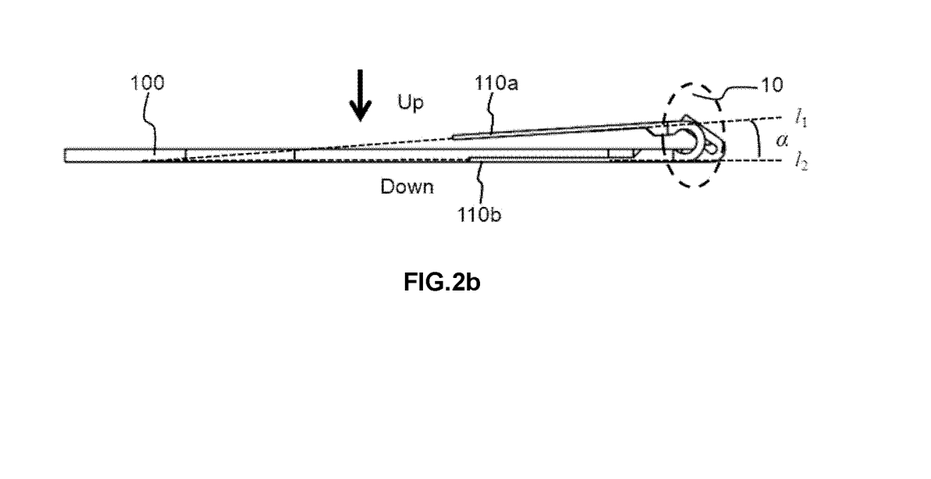
Figure 2C:
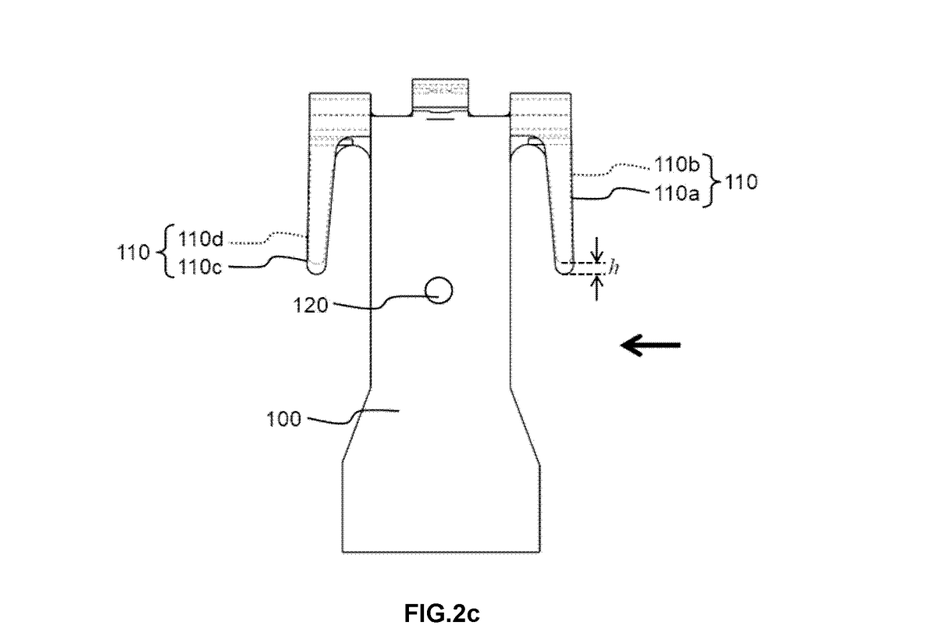

FIG. 2a, FIG. 2b, and FIG. 2c are respectively a schematic view of a three-dimensional, a side view, and a top view of the driving unit 100, and the top view direction of FIG. 2c is the direction indicated by the arrow in FIG. 2b, while the side view direction of FIG. 2b is the direction shown by the arrow in FIG. 2c.

In the embodiment of the present invention, the two driving arms 110 on one side of the driving unit 100 are installed up and down. Here, the up and down settings refer to the up and down positional relationship representations shown in FIG. 2b. Specifically, the two driving arms 110 (such as 110a and 110b) on the side of the driving unit 100 can be seen in the side view FIG. 2b, and in the top view FIG. 2c, 110b and 110d are blocked by 110a and 110c, respectively, wherein 110b and 110d are indicated by dotted lines in FIG. 2c.

In the embodiment of the present invention, since the driving wheel 130 is circular, the surfaces on which the adjacent teeth are applied with the engaging force are not parallel. Therefore, in order to keep the angle between the driving arms 110 and the teeth engaging surface 90 degree during engaging, thereby improving the engaging efficiency of the driving arms 110, when the driving arms 110 on one side of the driving unit 100 engage the wheel teeth 131, the lines representing the engaging directions of the two driving arms 110 intersect each other. Specifically, as shown in FIG. 2b, when the wheel teeth 131 are engaged by 110a and/or 110b, the straight line where 110a is located is $l_1$, the straight line where 110b is located is $l_2$, wherein the angle between $l_1$ and $l_2$ is $\alpha$, $3.1° \leq \alpha \leq 4.1°$. Specifically, in the embodiment of the present invention, $\alpha = 3.5°$. In another embodiment of the invention, $\alpha = 3.3°$. In still another embodiment of the invention, $\alpha = 3.9°$.

It should be noted that, in other embodiments of the present invention, according to different structural designs, when the driving arms 110 on one side of the driving unit 100 engage the wheel teeth 131, the lines representing the engaging directions of these two driving arms 110 can also be parallel ($\alpha = 0°$) or skew with a structure also able to drive the driving wheel 130 to rotate to achieve the purpose of drug infusion. In this case, the angle $\alpha$ between $l_1$ and $l_2$ may be set according to the actual structure, such as according to the diameter, number of the driving wheel 130, the number of the wheel teeth 131, the pitch of the screw 170, the positional relationship and the number of the driving arms 110. For example, a may be between $0° \sim 3.1°$ or $4.1° < \alpha \leq 7°$, and is not specifically limited herein.

Figure 3A:
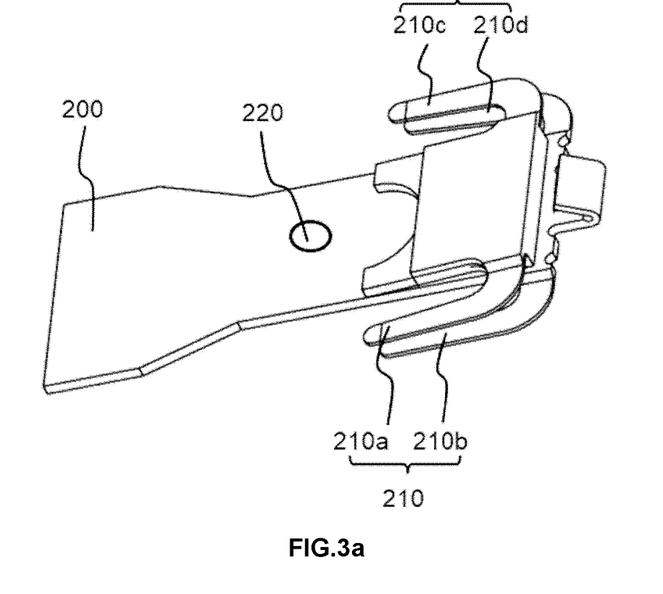
FIG. 3a-FIG. 3b are schematic structural view of a driving unit of a bilaterally driven drug infusion device with multiple infusion modes according to another embodiment of the present invention.
Figure 3B:
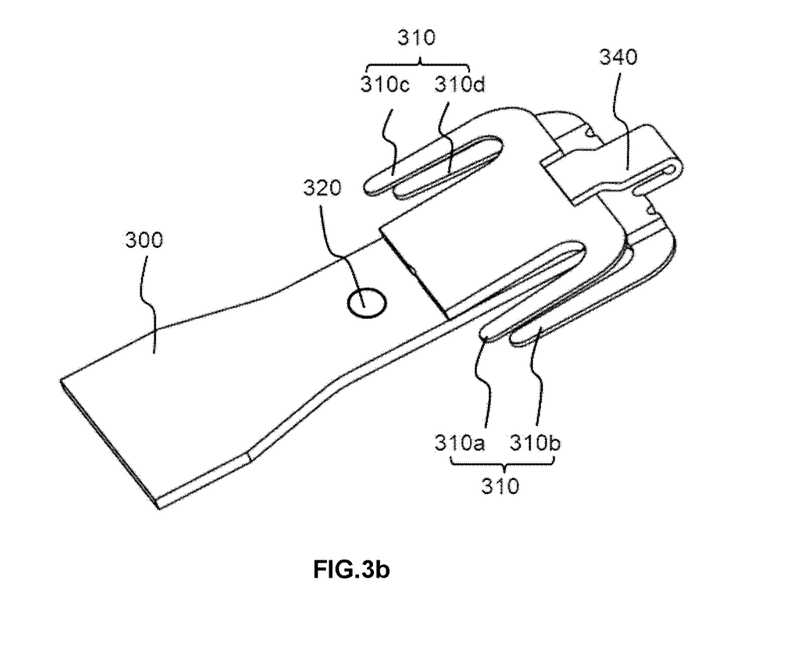

As shown in the dotted portion 10 of FIG. 2a and FIG. 2b, in the embodiment of the present invention, the two driving arms 110 on one side of the driving unit 100 are formed by folding at the dotted circle 10. In other embodiments of the present invention, the two driving arms 110 on one side of the driving unit 100 may also be formed by other means. As shown in the perspective view of the driving unit shown in FIG. 3a and FIG. 3b, the up position 210a, 210c and the down position 210b, 210d are respectively set in different structural subunits. As in FIG. 3a, the two structural subunits are secured together by welding or other means of attachment to form one single structure. And as shown in FIG. 3b, the two structural subunits are connected at the top position 340 of the driving unit 300, and then the top position 340 of the driving unit 300 is folded over to form the structure of the driving arms 310 in the embodiment of the present invention.

It should be noted that, in other embodiments of the present invention, the driving arms may be formed by other means, as long as the arms are able to drive the driving wheel to rotate, and is not specifically limited herein.

Figure 4:
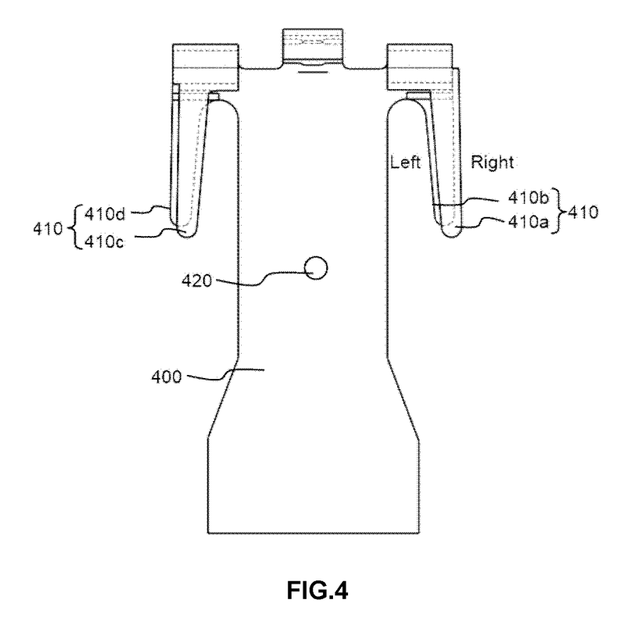
FIG. 4 is a schematic structural view of a driving unit in a bilaterally driven drug infusion device with multiple infusion modes according to another embodiment of the present invention.

Please refer to FIG. 4, which is a top view of a driving unit 400 according to another embodiment of the present invention.

The angles of view of FIG. 4 and FIG. 2c are the same. According to FIG. 2a, FIG. 2b, FIG. 2c and FIG. 4, it is apparent that the two driving arms on one side of the driving unit 400 are slightly offset from left and right, such as 410a, 410b and 410c, 410d. Specifically, in one embodiment of the invention, 410a and 410c are offset to the right and 410b and 410d are offset to the left.

It should be noted that, in other embodiments of the present invention, the left and right offset degree of the two driving arms on the same side and the direction in which the two are offset relative to each other need to be determined according to the actual structural design, and are not limited specifically described herein. Furthermore, in an embodiment of the invention, the two driving arms on one side of the driving unit can also be installed left and right. Here, the left and right installing mean that from the perspective of FIG. 4 (top view), two complete driving arms on one side of the driving unit can be seen, while from the perspective of FIG. 2b (side view), the driving arms close to the main body of the driving unit is completely or partially blocked by the driving arms away from driving unit's main body. In this case, the lines presenting the engaging directions of driving arms on the same side of driving unit is coplanar or skew. At the same time, there is no particular limitation on the length or the length relationship among different driving arms.

Figure 5:
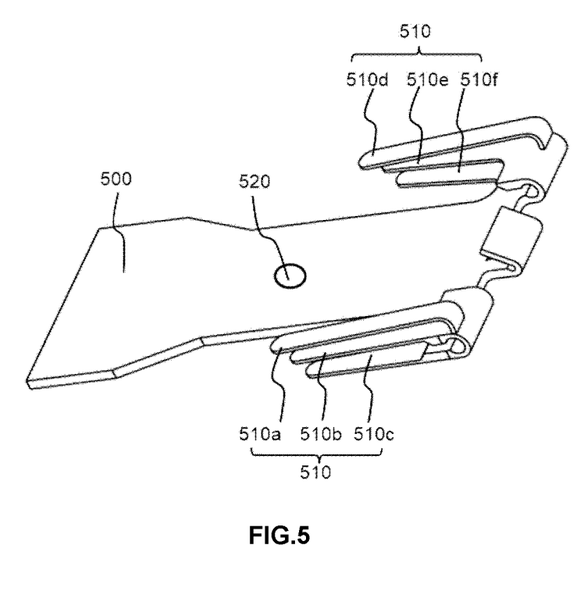
FIG. 5 is a schematic structural view of a driving unit in a bilaterally driven drug infusion device with multiple infusion modes according to another embodiment of the present invention.

Please refer to FIG. 5, which is a schematic perspective view of a driving unit 500 according to still another embodiment of the present invention.

Specifically, the driving unit 500 includes six driving arms 510, each three of which are installed on one side of the driving unit 500. Specifically, 510a, 510b, and 510c are installed on one side, and 510d, 510e, and 510f are installed on the other side. As described above, the lengths, the length relationships and the positional settings of the driving arms 510 on the same side are designed according to the specific structure and working principle, and are not specifically limited herein. Specifically, in the embodiment of the present invention, the positional relationship of the three driving arms 510 on the same side of the driving unit 500 is similar to that in FIG. 2a, FIG. 2b and FIG. 2c, that is, the three driving arms 510 on the same side of the driving unit 500 are installed up and down.

It should be noted that, in other embodiments of the present invention, the total number of driving arms may also be an odd number, such as three, five or more, that is, the numbers of driving arms on both sides of the driving unit are not equal. Moreover, the structural relationship between the different driving arms can be similar to that described above, and no specific restrictions are imposed here.

Referring to FIG. 6 and FIG. 2c together, FIG. 6 is a partial structural diagram of the driving wheel 130, and wheel teeth 131.

In the perspective of FIG. 2c, the horizontal distance between the driving ends of the two driving arms on one side of the driving unit 100 is h, and the pitch of the wheel teeth 131 is s, then $0.5s \leq h \leq 1.5s$. Specifically, in the embodiment of the present invention, h=0.8 s. In another embodiment of the invention, h=1.2 s. In still another embodiment of the invention, h=s. Here, the driving end of the driving arms 110 refers to the end of the driving arms 110 that directly contacts the wheel teeth 131 when engaged. The horizontal distance refers to the distance between two projection points of the driving ends of the two driving arms 110 on the same side of the driving unit 100 on a plane when viewed in an angle as shown in FIG. 2c.

It should be noted that in other embodiments of the present invention, $0.1 \text{ s} \le h < 0.5 \text{ s}$ or $1.5 \text{ s} < h \le 2.5 \text{ s}$ may be used, and the effects of the present invention may be also achieved, and also are not specifically limited herein.

As shown in FIG. 6, in the embodiment of the present invention, the driving wheel 130 is a ratchet, and the wheel teeth 131 are ratchet teeth. Each ratchet tooth surface includes a gentle surface and a steep surface, therefore it's easy to be engaged, as shown in FIG. 6. Moreover, in the embodiment of the present invention, the driving arms 110 of the driving unit 100 include a portion that drives the driving wheel 130 to rotate and a portion that does not drive the driving wheel 130 to rotate during the entire pivot of the driving unit 100 in one direction. The portion that drives the driving wheel 130 to rotate applies the engaging force on the steep surface of the ratchet teeth, in order to drive the driving wheel 130 to rotate in the C direction.

Please refer to FIG. 7, which is a schematic perspective view of the driving unit 100 and the driving wheel 130.

With reference to FIG. 7, FIG. 1, FIG. 2b and FIG. 2c, in the embodiment of the present invention, under the action of the power unit 180, the driving unit 100 pivots around the pivot shaft 120, thereby driving the plurality of driving arms 110 on both sides of the driving unit 100 to engage the wheel teeth 131 for rotation of the driving wheel 130.

Figure 8:
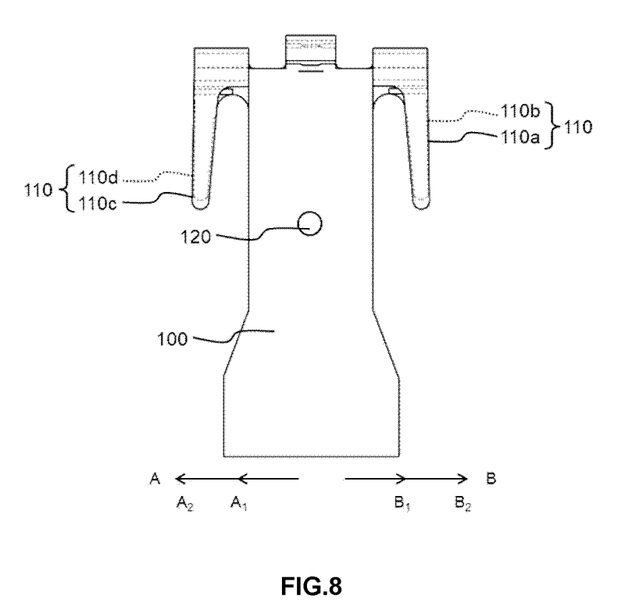
FIG. 8 is a schematic structural view showing a pivoting position of different movement modes of a driving unit in a bilaterally driven drug infusion device with multiple infusion modes according to an embodiment of the present invention.

Referring to FIG. 7 and FIG. 8 together, FIG. 8 is a schematic structural diagram of the adjustable pivoting movements of the driving unit 100

As described above, the driving unit 100 has a certain distance h between the driving ends of the driving arms 110 on the same side, and there is a certain angle α between the lines representing the driving directions when the arms are engaged. And therefore, the driving unit 100 pivots in one direction in a single time throughout the process, as shown in FIG. 7 in a single pivot in the direction A, 110a and/or 110b engage the wheel teeth 131 to drive the driving wheel 130, while 110c and 110d can slide on the wheel teeth 131 (as on the gentle surface of the ratchet teeth, but not exert a force for driving the driving wheel 130 to rotate). And obviously, 110c slides to the next driving position first. Here, the driving position refers to the position where the driving arm can engage the wheel teeth to advance, so as to the following driving position. At this time, the driving end of 110c acts on the steep surface of the ratchet teeth. At this time, the driving unit 100 stops pivoting and the driving arms 110a and/or 110b stop engaging the wheel teeth 131, and the driving wheel 130 stops rotating. Thus the driving unit 100 completes one step of pivot. Referring to FIG. 8, the driving unit 100 pivots in the A direction to reach $A_1$ position, which corresponds to one kind of pivot amplitude, making the infusion device have an infusion increment. The next moment the driving unit 100 continues to pivot in the A direction, 110d will slide to the next driving position. Similarly, the driving end of 110d also acts on the steep surface of the ratchet teeth. Thus the driving unit 100 completes a second step of pivot. Referring to FIG. 8, the driving unit 100 still pivots in the A direction to reach $A_2$ position, which corresponds to another kind of pivot amplitude, making the infusion device have another infusion increment. At this time, 110c and 110d respectively complete the sliding between adjacent wheel teeth 131, and the driving unit 100 completes the whole process of single pivot in the A direction, reaching $A_1$ and $A_2$ positions respectively, thereby driving the driving wheel 130 to rotate by two steps, realizing two-step infusion of the drug device and making the infusion device have two different infusion increments.

It should be noted that, in the above pivoting process, 110d may first slide to the next wheel teeth 131, and then 110c slide to the next wheel teeth 131, which is not specifically limited herein. Similarly, when the driving unit 100 pivots in the B direction, it can reach $B_1$ and $B_2$ positions respectively, which also corresponds another two infusion increments.

Obviously, in the whole process of the above-mentioned single pivot in the A direction, the driving unit 100 undergoes an alternate action of pivot and stop, and the driving arms 110 alternately engage and stop engaging wheel teeth 131 to drive the driving wheel 130 to rotate and stop rotating, realizing two-step rotation of the driving wheel, and finally achieves two-level increment-adjustable drug infusion.

Specifically, when the driving unit has two driving arms on one side, the driving unit undergoes two-step movement of the pivot-stop-pivot-stop during the single pivot in the A direction, in order to drive driving wheel for two-step rotation. When the driving unit has three driving arms on one side, the driving unit performs the pivot-stop-pivot-stop-pivot-stop three-step motion in the whole process of single pivot in the A direction, realizing three-step rotation of the driving wheel to achieve three-level increment-adjustable drug infusion. By analogy, when there are more driving arms on one side of the driving unit, the driving unit realizes multiple-step driving of the driving wheel by the multiple-step actions of the pivot-stop-pivot-stop-pivot- . . . -pivot-stop, completing multi-level increment-adjustable drug infusion.

With continued reference to FIG. 7, in combination with the above, in the embodiment of the present invention, when the driving unit 100 drives the driving wheel 130 to rotate, at least one of the driving arms 110 on the driving force side applies an engaging force to the wheel teeth 131. While one or both of the driving arms 110 on the other side are in contact with the wheel teeth 131 without applying any force to the wheel teeth 131 to drive the driving wheel 130 to rotate. Therefore, there is a case in the embodiment of the present invention that only one of the driving arms 110 of the driving unit 100 engages the wheel teeth 131 to rotate the driving wheel 130, and the other driving arms 110 are in contact with the driving wheel 130 without applying any force to the wheel teeth 131 to rotate the driving wheel 130.

It should be noted that, in the embodiment of the present invention having three or more driving arms on one side of the driving unit, when the driving unit is in operation, the above-mentioned similar situation may also occur. When there are an odd number of driving arms, the numbers of driving arms on both sides of the driving unit are not equal, and the same process as above is also performed in the whole process of the driving unit rotating in a certain direction.

Referring to FIG. 8 again, in another embodiment of the present invention, when the driving unit 100 has two driving arms 110 on one side, the driving unit 100 pivots one step in the A direction, that is, reaching the $A_1$ position, and then pivots one or two steps in the B direction, that is, reaching the $B_1$ or $B_2$ position until the pivot in the B direction stops, the driving unit 100 pivoting by different amplitudes. This process completes the alternate pivot of the driving unit 100 in two directions, so that the driving wheel 130 can be rotated in multiple steps. Therefore, in the embodiment of the present invention, the driving unit 100 can alternately switch modes among $A_1$-$B_1$ or $A_1$-$B_1$-$B_2$ or $B_1$-$A_1$-$A_2$, so as to achieve the purpose of switching among different increments of infusion.

With continued reference to FIG. 8, in another embodiment of the present invention, the driving unit 100 can also be pivoted directly to the $A_2$ position without passing through the $A_1$ position, then directly pivoted to the $B_2$ position without passing through the $B_1$ position, that is, the driving unit 100 alternately pivots between the $A_2$-$B_2$ positions. As described above, the driving unit 100 can also alternately pivot between the $A_1$-$B_1$ positions. Obviously, in a unit time, the dosage of infused drug when the driving unit 100 alternately pivots between the $A_2$-$B_2$ positions is greater than the dosage of infused drug when it alternately pivots between the $A_1$-$B_1$ positions.

In other embodiments of the present invention, as shown in FIG. 8, after the driving unit 100 pivots in the direction A and the driving arm 110c or 110d slides to the driving position, the driving unit 100 may continue to pivot in the direction A until both the driving arm 110c and 110d are away from the driving position, the driving unit 100 stopping pivoting and starting to pivot in the B direction at the next moment. This operation mode enables the driving unit 100 to have more kinds of movement amplitudes, that is, multiple-mode pivot. Obviously, when the driving unit 100 pivots in the direction B for a certain period of time, all the driving arms 110 slide on the surface of the wheel teeth 131, that is, no engaging is performed. For ease of description, the above process will be described in detail below in conjunction with an embodiment in which the driving unit 100 includes only two driving arms.

Figure 9A:
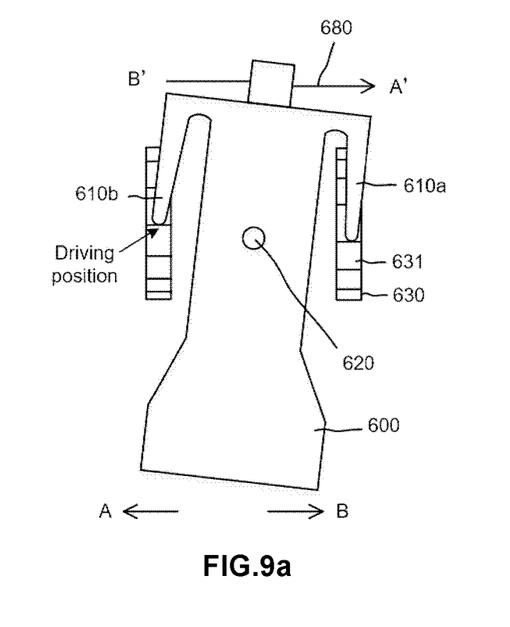
FIG. 9a-FIG. 9c are schematic structural views of a driving unit including two driving arms in a bilaterally driven multi-infusion mode drug infusion device according to an embodiment of the present invention.
Figure 9B:
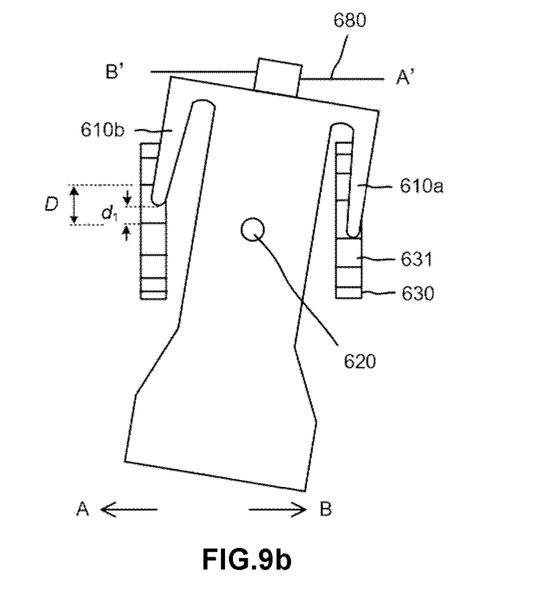
Figure 9C:
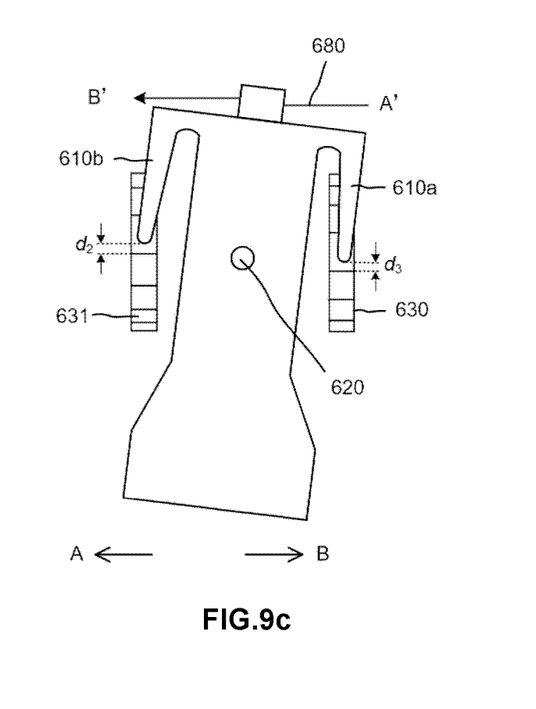

FIG. 9a-FIG. 9c are schematic structural views of the driving unit 600 including two driving arms 610a and 610b.

Similar to the driving principle described above, in one embodiment of the present invention, when the power unit 680 applies force to the driving unit 600 in the A' direction, the driving arm 610a engages the wheel teeth 631 forward, making the driving unit 600 pivot around the pivot shaft 620 and the driving arm 610b sliding on the surface of the wheel teeth 631 until the driving arm 610b reaches the driving position, in which the driving unit 600 pivots by a certain amplitude, as shown in FIG. 9a. The power unit 680 starts to apply force in the B' direction, making the driving arm 610b engage the wheel teeth 631 forward. By analogy, the driving unit 600 alternately pivots in two directions.

In the embodiment of the present invention, after the driving arm 610b reaches the driving position, the driving unit 600 continues to pivot in the direction A, thus the driving arm 610b continuing to slide on the surface of the wheel teeth 631. After the distance between the driving end of the driving arm 610b and the steep surface of the wheel teeth 631 is $d_1$, the power unit 680 stops outputting force, which is shown in FIG. 9b. At this time, the driving unit 600 pivots by a larger amplitude. If the pitch of the wheel tooth is D, then $d_1 = D/n$, $n > 1$. Obviously, after the power unit 600 outputs force in the direction of B', both the driving arms 610b and 610a slide on the surface of the wheel teeth 631 within a period of time after the driving unit 600 starts to pivot, as shown in FIG. 9c. The distances between the driving arms 610b, 610a and the steep surfaces of their corresponding wheel teeth 631 are $d_2$ and $d_3$, respectively. Obviously, $d_2 < D$ and $d_3 < D$. As described above, when more driving arms are provided on the driving unit 600, a similar situation will occur for each driving arm.

The total distance of the driving arm 610b sliding in the above process can be arbitrarily selected, for example, the total sliding distance is 0.4 D, 0.7 D, D (as shown in FIG. 9a), 1.5 D, 1.75 D, 2 D, 2.3 D, 2.5 D, etc. The driving unit 600 has various pivot amplitudes, that is, various rotation gears, making the infusion device have multiple infusion increments.

Figure 10A:
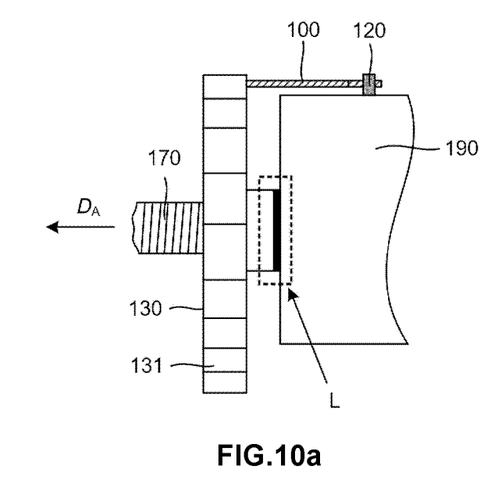
FIG. 10a-FIG. 10b are schematic structural views of a driving wheel and a base or a limiting member in a bilaterally driven multi-infusion mode drug infusion device according to an embodiment of the present invention.
Figure 10B:
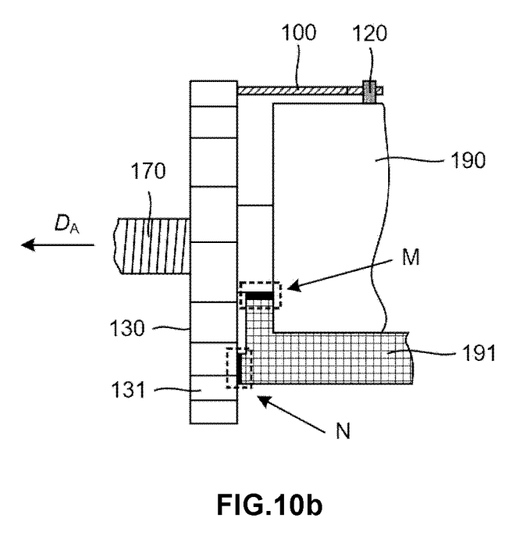

FIG. 10a and FIG. 10b are schematic diagrams of the driving wheel 130 and the base 190, or the position limited member 191 according to an embodiment of the present invention. FIG. 10a and FIG. 10b are front views of partial structures in FIG. 1.

When the driving arm 110 slides on the surface of the wheel teeth 131, the driving arm 110, contact with the wheel teeth 131, applies a certain pressure to the driving wheel 130 to ensure the non-rotating of the driving wheel 130. However, it is obvious that due to the structural features of the wheel teeth 131 and the circumference of the driving wheel 130, the pressure applied by the driving arm 110 is not equal at different positions. Therefore, when the driving arm 110 slides (including reset movement or sliding forward) on the surface of the wheel teeth 131, the driving wheel 130 may rotate forward or reverse, which affects the accuracy of the drug infusion volume and brings safety risk.

As shown in FIG. 10a, the driving wheel 130 is movably assembled on the base 190 remaining in frictional engagement. Here, the friction fit between these two means a certain friction force preset between two mutually moving structures, so as to the meaning of the following friction fit. In the embodiment of the present invention, the frictional force of the relative movement between the driving wheel 130 and the base 190 is applied or increased at the position L, indicated by the dotted frame, to ensure that when the driving arm 110 slides on the surface of the wheel teeth 131, the driving wheel 130 stops rotating.

As shown in FIG. 10b, in another embodiment of the present invention, the infusion device further includes a position limited member 191 that is movably assembled on the base 190 to limit the position of the driving wheel 130. The position limited member 191 is in friction fit with the driving wheel 130 at position M or position N, indicated by the dotted frame. Similarly, in the embodiment of the present invention, the position limited member 191 increases the frictional force that the driving wheel 130 receives when rotating, also ensuring that the driving wheel 130 stops rotating when the driving arm 110 slides on the surface of the wheel teeth 131. At the same time, the position limited member 191 can make full use of the internal space of the infusion device, and frictionally cooperate with the driving wheel 130 at multiple positions.

Other embodiments of the present invention do not limit the position of the above friction fit, as long as the condition for applying or increasing the friction force received by the second driving unit during movement is satisfied. For example, the friction force can also be applied on both sides of the driving wheel 130 at the same time. The embodiment of the present invention neither limits the material of the position limited member 191. For example, the position limited member 191 is an elastic member, a plastic member or a metal member.

Other embodiments of the present invention may increase the pressure of the driving arm 110 on the wheel teeth 131 instead of providing the above-mentioned friction fit, which can increase the maximum static friction of the driving wheel 130 and also ensure the non-rotating of the driving wheel 130 when the driving arm 110 slides on the surface of the wheel teeth 131.

If the minimum dosage of infused drug driven by the driving unit is the minimum increment of the infusion device, the bilaterally driven drug infusion device with multiple infusion modes using the embodiment of the present invention can reduce the minimum increment of drug dosage and achieve more precise control of the drug infusion. When the patient needs to infuse more drugs, the large $A_2$-$B_2$ mode can be selected to speed up the infusion rate. When a small amount of drug needs to be infused, the patient can select the small $A_1$-$B_1$ mode to reduce the drug infusion rate and achieve precise control of the drug infusion.

Compared with the device with increment-unadjustable infusion, in the bilaterally driven drug infusion device with multiple infusion modes, the driving unit performs multiple-mode operation, making the infusion device have multiple infusion increments or infusion rates. With the bilaterally driven drug infusion device with multiple infusion modes of the embodiment of the invention, the patient can freely and flexibly switch between different increments of infusion according to the actual drug dosage and the demand of the infusion rate, thereby improving the infusion efficiency. At the same time, intermediate $A_1$-$B_1$-$B_2$ mode or $B_1$-$A_1$-$A_2$ mode and the small $A_1$-$B_1$ mode are set along with the large $A_2$-$B_2$ mode. And the bilaterally driven drug infusion device with multiple infusion modes can reduce the minimum dosage of infused drug in order to achieve the goal of precise control of the infusion.

As with the bilaterally driven drug infusion device with multiple infusion modes of the embodiment of the present invention, when the infusion is started, the amount of drug required is relatively large, and the patient can select the large $A_2$-$B_2$ mode shown in FIG. 8 for infusion. After a period of infusion, the intermediate $A_1$-$B_1$-$B_2$ mode or $B_1$-$A_1$-$A_2$ mode can be used to reduce the rate of drug infusion. When the drug infusion is about to be completed, the patient can switch to the small $A_1$-$B_1$ mode to further reduce the infusion rate and achieve precise control of the drug infusion. Of course, the patient can also choose one or several of the modes for infusion, and there are no specific restrictions.

In other embodiments of the present invention, when more than two driving arms are installed on one side of the driving unit, the infusion device can have more and more elaborate infusion modes, and the patient can further flexibly control the infusion to make the infusion process more precisely.

In summary, the present invention discloses a bilaterally driven drug infusion device with multiple infusion modes, in which the driving unit performs multiple-mode operations, thereby making the infusion device have multiple infusion increments or infusion rates, realizing increment-adjustable drug infusion, increasing the patient's flexibility in controlling the infusion process and improving the efficiency of drug infusion. At the same time, the bilaterally driven drug infusion device with multiple infusion modes also reduces the minimum dosage of infused drug, from which the patients can accurately control the drug infusion and precisely manage their own physiological condition.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A bilaterally driven drug infusion device with multiple infusion modes, comprising:
   a drug storage unit;
   a piston and a driving wheel respectively connected with a screw, the driving wheel, drives the screw to move by rotation, the piston is arranged in the drug storage unit, the screw advances the piston to move;
   a driving unit cooperating with the driving wheel; and
   a power unit, connected to the driving unit, outputs forces in two different directions on the driving unit to lead the driving unit to perform multiple-mode operations, making the bilaterally driven drug infusion device have multiple infusion increments or infusion rates,
   wherein the bilaterally driven drug infusion device further comprising a pivot shaft, the driving wheel comprises two sub-wheels, provided with wheel teeth, the pivot shaft is disposed between the two sub-wheels, the driving unit pivots around the pivot shaft, each of both sides of the driving unit is provided with a plurality of driving arms, and the driving arms at each of the both sides of the driving unit rotate one of the two sub-wheels by engaging the wheel teeth.

2. The bilaterally driven drug infusion device with multiple infusion modes of claim 1, wherein an operation of the driving unit includes a movement amplitude or a movement rate, therefore, the multiple-mode operations of the driving unit include multiple movement amplitudes or multiple movement rates.

3. The bilaterally driven drug infusion device with multiple infusion modes of claim 1, wherein one of the multiple movement amplitudes corresponds to one kind of pivot mode of the driving unit, and the driving unit, pivoting in various pivot modes, drives the driving arms to rotate the driving wheel to implement increment-adjustable infusions, and each of the increment-adjustable infusions corresponds to an infusion increment.

4. The bilaterally driven drug infusion device with multiple infusion modes of claim 3, wherein multiple-mode pivot of the driving unit includes: after pivoting one or more steps in one direction in a single time, the driving unit starts pivoting one or more steps in another direction until an end of the pivot in this direction, the driving unit completes an alternate pivot in both of the directions to perform multiple-mode driving on the driving wheel.

5. The bilaterally driven drug infusion device with multiple infusion modes of claim 4, wherein the driving arms at each of the both sides of the driving unit comprises two driving arms, and the two driving arms at each of the both sides of the driving unit at least partially overlap with each other along an extension direction of the pivot shaft.

6. The bilaterally driven drug infusion device with multiple infusion modes of claim 5, wherein each of the two driving arms at each of the both sides of the driving unit comprises an end for pushing the corresponding sub-wheel, a distance between the end of one of the two driving arms at each of the both sides of the driving unit projected onto a plane where an other one of the two driving arms exists and the end of the other one of the two driving arms is h, a pitch of the wheel teeth is s, $0.1s \leq h \leq 2.5s$.

7. The bilaterally driven drug infusion device with multiple infusion modes of claim 6, wherein $0.5s \leq h \leq 1.5s$.

8. The bilaterally driven drug infusion device with multiple infusion modes of claim 4, wherein the wheel teeth are ratchet teeth, and during a whole process of the driving unit pivoting in the direction, the driving unit alternately pivots and stops for multiple times to drive the driving arms to alternately engage and stop engaging the ratchet teeth, so that the driving wheel alternately rotates and stops rotation to perform tooth number adjustable rotation.

9. The bilaterally driven drug infusion device with multiple infusion modes of claim 8, wherein when the driving unit drives the driving wheel, at least one of the driving arms on one of the both sides engages the wheel teeth, while one of the driving arms on the other of the both sides of the driving unit slides on the wheel teeth.

10. The bilaterally driven drug infusion device with multiple infusion modes of claim 1, wherein multiple-mode pivot of driving unit includes: a large mode and a small mode, and when an infusion is performed, the driving unit switches between the large mode and the small mode to realize an increment-adjustable infusion.

11. The bilaterally driven drug infusion device with multiple infusion modes of claim 10, wherein the multiple-mode pivot of the driving unit further includes: one intermediate mode or more intermediate modes, wherein the intermediate mode is between the large mode and the small mode, and the driving unit switches among the large mode, the intermediate mode and the small mode to achieve the increment-adjustable infusion.

12. The bilaterally driven drug infusion device with multiple infusion modes of claim 9, further comprising a base on which the driving wheel is movably assembled, wherein the base and the driving wheel are frictional fit, and the driving wheel stops rotating when the driving arm is sliding on a surface of the wheel teeth.

13. The bilaterally driven drug infusion device with multiple infusion modes of claim 12, further comprising a position limited member which is movably assembled on the base to limit a position of the driving wheel, and the position limited member and the driving wheel are frictional fit, and the driving wheel stops rotating when all of the driving arms are sliding on the surface of the wheel teeth.

* * * * *